(12) United States Patent
Stumpf et al.

(10) Patent No.: US 12,303,258 B2
(45) Date of Patent: May 20, 2025

(54) HEARING DEVICE-BASED SYSTEMS AND METHODS FOR DETERMINING A HEART RATE VALUE

(71) Applicant: SONOVA AG, Staefa (CH)

(72) Inventors: Nina Stumpf, Maennedorf (CH); Evgeny Murtola, Dübendorf (CH); Nadim El Guindi, Zürich (CH); Niklas Ignasiak, Zürich (CH); Anna M. Parker, Basel (CH); Nicholas Ohs, Zürich (CH); Manuela Feilner, Egg b. Zürich (CH); Hans-Ueli Roeck, Hombrechtikon (CH)

(73) Assignee: Sonova AG, Staefa (CH)

( * ) Notice: Subject to any disclaimer, the term of this patent is extended or adjusted under 35 U.S.C. 154(b) by 660 days.

(21) Appl. No.: 17/588,573

(22) Filed: Jan. 31, 2022

(65) Prior Publication Data

US 2023/0240560 A1 Aug. 3, 2023

(51) Int. Cl.
*A61B 5/12* (2006.01)
*A61B 5/00* (2006.01)
*A61B 5/024* (2006.01)
*A61B 5/11* (2006.01)
*A61B 5/16* (2006.01)

(52) U.S. Cl.
CPC ............ *A61B 5/125* (2013.01); *A61B 5/024* (2013.01); *A61B 5/1118* (2013.01); *A61B 5/165* (2013.01); *A61B 5/6815* (2013.01); *A61B 5/7475* (2013.01)

(58) Field of Classification Search
CPC ....... A61B 5/125; A61B 5/024; A61B 5/1118; A61B 5/165; A61B 5/6815; A61B 5/6817; A61B 5/7475
See application file for complete search history.

(56) References Cited

U.S. PATENT DOCUMENTS

| 9,848,823 | B2 * | 12/2017 | Raghuram | ........... A61B 5/7246 |
| 11,109,809 | B2 | 9/2021 | Leboeuf | |
| 2015/0374240 | A1 * | 12/2015 | Lee | ........... A61B 5/024 600/483 |
| 2019/0373377 | A1 * | 12/2019 | Larsen | ........... A61B 5/6817 |
| 2024/0285190 | A1 * | 8/2024 | Bhowmik | ........... A61B 5/112 |

FOREIGN PATENT DOCUMENTS

| CN | 104207756 | 12/2014 |
| CN | 105943016 | 9/2016 |
| WO | 2017028149 | 2/2017 |
| WO | 2019133491 | 7/2019 |
| WO | 2021046237 | 3/2021 |

* cited by examiner

*Primary Examiner* — Eric F Winakur
(74) *Attorney, Agent, or Firm* — ALG Intellectual Property, LLC

(57) ABSTRACT

An illustrative hearing system may be configured to receive, from a motion sensor included in a hearing device configured to be worn by a user, motion data representative of motion of the user while the user wears the hearing device and an output signal generated by a heart rate sensor in contact with the user. The hearing system may be further configured to determine, based the motion data, a heart rate probability distribution function and to determine, based on the output signal and the heart rate probability distribution function, a heart rate value for the user.

19 Claims, 7 Drawing Sheets

HEARING DEVICE-BASED SYSTEMS AND METHODS FOR DETERMINING A HEART RATE VALUE

BACKGROUND INFORMATION

A hearing device may enable or enhance hearing by a user wearing the hearing device by providing audio content received by the hearing device to the user. For example, a hearing aid may provide an amplified version of the audio content to the user to enhance hearing by the user. As another example, a sound processor included in a cochlear implant system may provide electrical stimulation representative of the audio content to the user to enable hearing by the user.

In some situations, a hearing device user may also utilize a heart rate sensor (e.g., a heart rate sensor integrated into the hearing device) to monitor a heart rate of the user. Unfortunately, however, movement of the user may affect the accuracy of the heart rate sensor.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
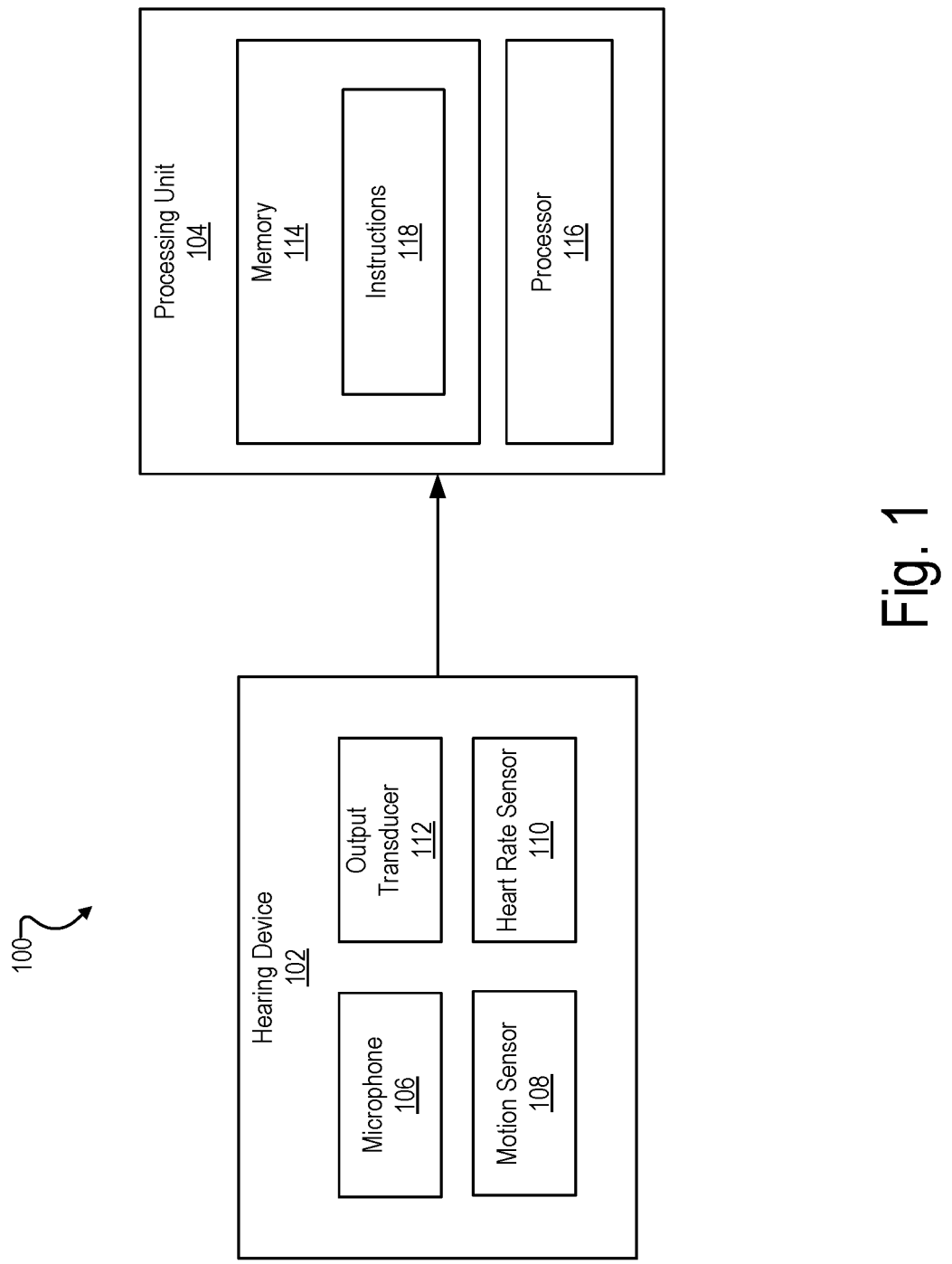
FIG. 1 shows an illustrative implementation of a hearing system.

An illustrative method, which may be performed by a hearing system, may include determining a heart rate value of a user based on motion data representative of motion of the user that may be received from a motion sensor included in a hearing device configured to be worn by a user. The hearing system, when performing the method, may further be configured to determine the heart rate value based on a heart rate probability distribution function representative of a probability of occurrence of the heart rate value during the motion of the user.

For example, the hearing system may be configured to receive, from a motion sensor included in a hearing device configured to be worn by a user, motion data representative of motion of the user while the user wears the hearing device; receive an output signal generated by a heart rate sensor in contact with the user; determine, based on the motion data, a heart rate probability distribution function; and determine, based on the output signal and the heart rate probability distribution function, a heart rate value for the user. For instance, the hearing system may be implemented as the hearing device, or as the hearing device and a computing device communicatively coupled to the hearing device. E.g., the system may comprise a memory storing instructions and a processor communicatively coupled to the memory, which may be included in the hearing device and/or the communication device, wherein the processor is configured to execute the instructions to perform the method.

The principles described herein may result in improved hearing systems compared to conventional systems that are not configured to determine a heart rate value based on motion data and/or a heart rate probability distribution function, as well as provide other benefits as described herein. For example, a hearing system configured to determine a heart rate value based on a heart rate probability distribution function associated with motion of the user may provide a more accurate heart rate value for the user. Moreover, a hearing system configured to determine a heart rate value based on a heart rate probability distribution function associated with motion of the user may allow the hearing system to be more computationally efficient by adjusting one or more settings of the hearing system and/or performing other operations. For example, the hearing system may abstain from taking a heart rate measurement and/or disable the device generating the heart rate measurement.

Various embodiments will now be described in more detail with reference to the figures. The systems, hearing devices, and methods described herein may provide one or more of the benefits mentioned above and/or various additional and/or alternative benefits that will be made apparent herein. While embodiments for a hearing system configured to determine a heart rate value are described below, the described embodiments may further be configured to determine a quality level for other measurements of user conditions (e.g., blood pressure) that may be affected by motion of the user.

FIG. 1 shows an illustrative implementation 100 of a hearing system configured to determine a heart rate value based on a heart rate probability distribution function associated with motion of the user. As shown, implementation 100 includes a hearing device 102 communicatively coupled with a processing unit 104. Implementation 100 may include additional or alternative components as may serve a particular implementation.

Hearing device 102 may be implemented by any type of hearing device configured to enable or enhance hearing by a user wearing hearing device 102. For example, hearing device 102 may be implemented by a hearing aid configured to provide an amplified version of audio content to a user, a sound processor included in a cochlear implant system configured to provide electrical stimulation representative of audio content to a user, a sound processor included in a bimodal hearing system configured to provide both amplification and electrical stimulation representative of audio content to a user, or any other suitable hearing prosthesis.

As shown, hearing device 102 includes a microphone 106, a motion sensor 108, a heart rate sensor 110, and an output transducer 112. Hearing device 102 may include additional or alternative components as may serve a particular implementation.

Microphone 106 may be implemented by one or more suitable audio detection devices configured to detect an audio signal presented to a user of hearing device 102. The audio signal may include, for example, audio content (e.g., music, speech, noise, etc.) generated by one or more audio sources included in an environment of the user. Microphone 106 may be included in or communicatively coupled to hearing device 102 in any suitable manner. Output transducer 112 may be implemented by any suitable audio output device, for instance a loudspeaker of a hearing device or an output electrode of a cochlear implant system.

Motion sensor 108 may be implemented by any suitable sensor configured to detect motion of hearing device 102 and output motion data representative of the motion of hearing device 102. For example, motion sensor 108 may include any suitable inertial sensor (e.g., an inertial measurement unit (IMU), an accelerometer, a gyroscope, etc.). While hearing device 102 is being worn by a user, the motion data output by motion sensor 108 of hearing device 102 may be representative of motion by the user. In some examples, motion sensor 108 is included in hearing device 102. Alternatively, motion sensor 108 may be included in a different device (e.g., a watch or a mobile device worn or carried by the user). In these alternative configurations, hearing device 102 may access motion data generated by motion sensor 108 by being communicatively coupled to the different device.

Heart rate sensor 110 may be implemented by any suitable sensor configured to detect a heart rate of the user and output heart rate data representative of one or more heart rate values of the user. For example, heart rate sensor 110 may include an optical sensor (e.g., a photoplethysmography (PPG) sensor) and/or an electrical sensor (e.g., an electrocardiogram (ECG) sensor). In some examples, heart rate sensor 110 is included in hearing device 102 to position at least a portion of heart rate sensor 110 in sufficient contact with the user for generating heart rate data. Alternatively, heart rate sensor 110 may be included in a different wearable device separate from hearing device 102 (e.g., a watch or a mobile device worn or carried by the user). In these alternative configurations, hearing device 102 may access heart rate data generated by heart rate sensor 110 by being communicatively coupled to the different device.

Processing unit 104 may be implemented by one or more computing devices and/or computer resources (e.g., processors, memory devices, storage devices, etc.) as may serve a particular implementation. For example, processing unit 104 may be implemented by a mobile device, personal computer, and/or other computing device configured to be communicatively coupled (e.g., by way of a wired and/or wireless connection) to hearing device 102. As shown, processing unit 104 may include, without limitation, a memory 114 and a processor 116 selectively and communicatively coupled to one another. Memory 114 and processor 116 may each include or be implemented by computer hardware that is configured to store and/or process computer software. Various other components of computer hardware and/or software not explicitly shown in FIG. 1 may also be included within processing unit 104. In some examples, memory 114 and/or processor 116 may be distributed between multiple devices and/or multiple locations as may serve a particular implementation.

Memory 114 may store and/or otherwise maintain executable data used by processor 116 to perform any of the functionality described herein. For example, memory 114 may store instructions 118 that may be executed by processor 116. Memory 114 may be implemented by one or more memory or storage devices, including any memory or storage devices described herein, that are configured to store data in a transitory or non-transitory manner. Instructions 118 may be executed by processor 116 to cause processing unit 104 to perform any of the functionality described herein. Instructions 118 may be implemented by any suitable application, software, code, and/or other executable data instance. Additionally, memory 114 may also maintain any other data accessed, managed, used, and/or transmitted by processor 116 in a particular implementation.

Processor 116 may be implemented by one or more computer processing devices, including general purpose processors (e.g., central processing units (CPUs), digital signal processors (DSPs), graphics processing units (GPUs), microprocessors, etc.), special purpose processors (e.g., application specific integrated circuits (ASICs), field-programmable gate arrays (FPGAs), etc.), image signal processors, or the like. Using processor 116 (e.g., when processor 116 is directed to perform operations represented by instructions 118 stored in memory 114), processing unit 104 may perform various operations as described herein.

Figure 2:
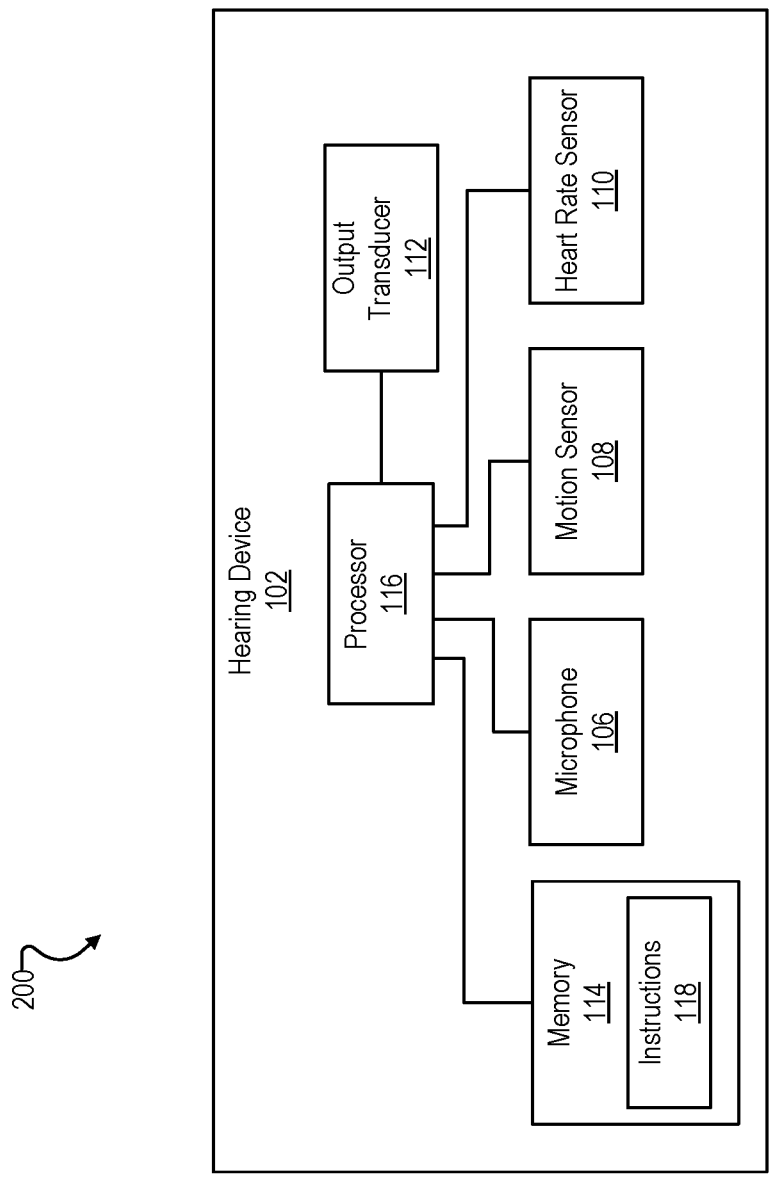
FIG. 2 shows another illustrative implementation of a hearing system.

FIG. 2 shows another illustrative implementation 200 of a hearing system configured to determine a heart rate value based on a heart rate probability distribution function associated with motion of the user. As shown, implementation 200 is similar to implementation 100, except that implementation 200 includes processor 116 and memory 114 located within hearing device 102. Implementation 200 may include additional or alternative components as may serve a particular implementation.

Figure 3:
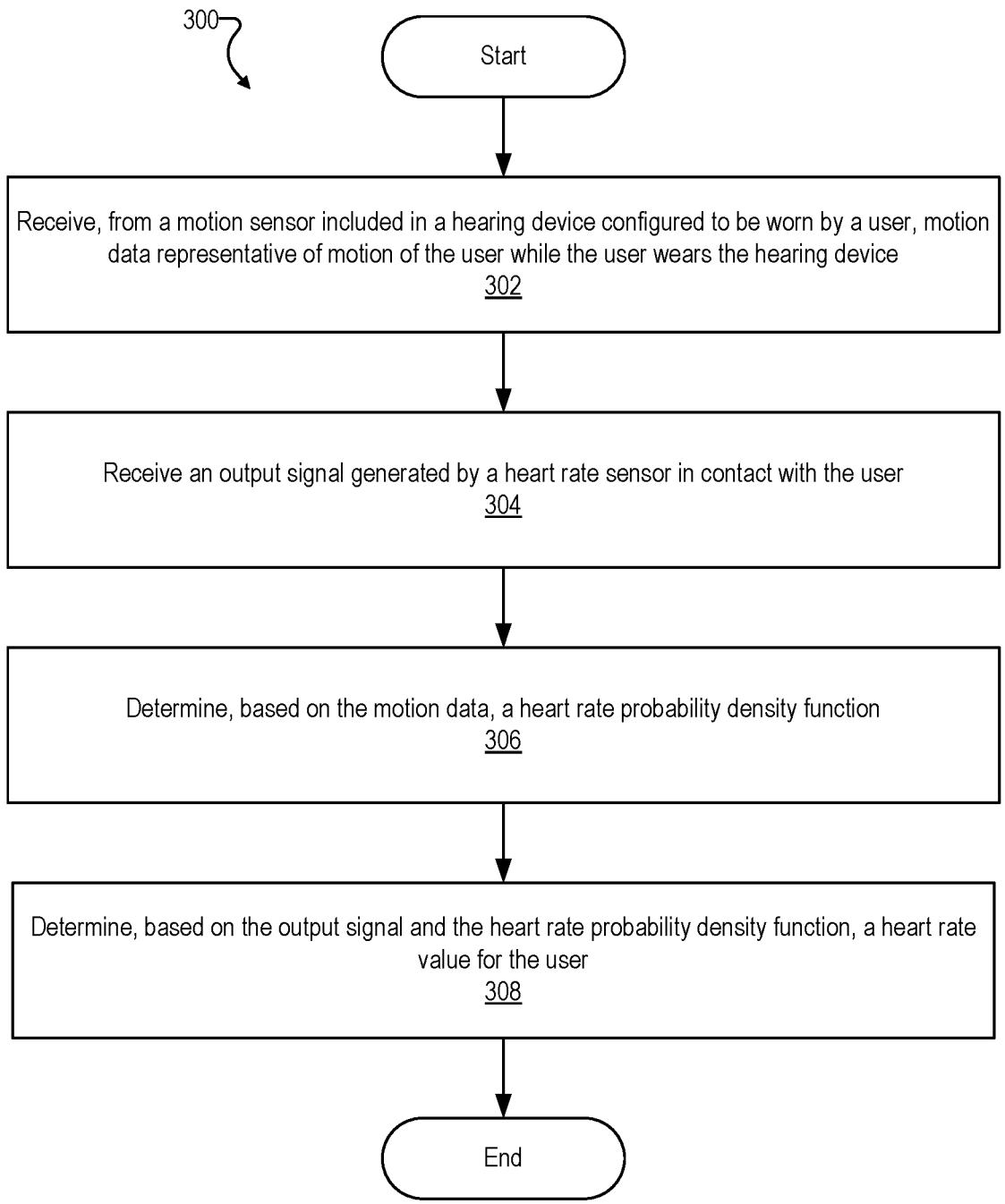
FIG. 3 shows an illustrative method of operating a hearing system.

FIG. 3 shows an illustrative method 300 that may be performed by a hearing system according to the principles described herein. While FIG. 3 illustrates exemplary operations according to one embodiment, other embodiments may omit, add to, reorder, and/or modify any of the operations shown in FIG. 3. Moreover, each of the operations depicted in FIG. 3 may be performed in any of the ways described herein.

As shown, a hearing system may, at operation 302, receive, from motion sensor 108 included in hearing device 102 configured to be worn by a user, motion data representative of motion of the user while the user wears hearing device 102. The hearing system may, at operation 304, receive an output signal generated by heart rate sensor 110 in contact with the user. The hearing system may, at operation 306, determine, based on the motion data, a heart rate probability distribution function. The hearing system may, at operation 308, determine, based on the output signal and the probability distribution function, a heart rate value for the user.

Figure 4:
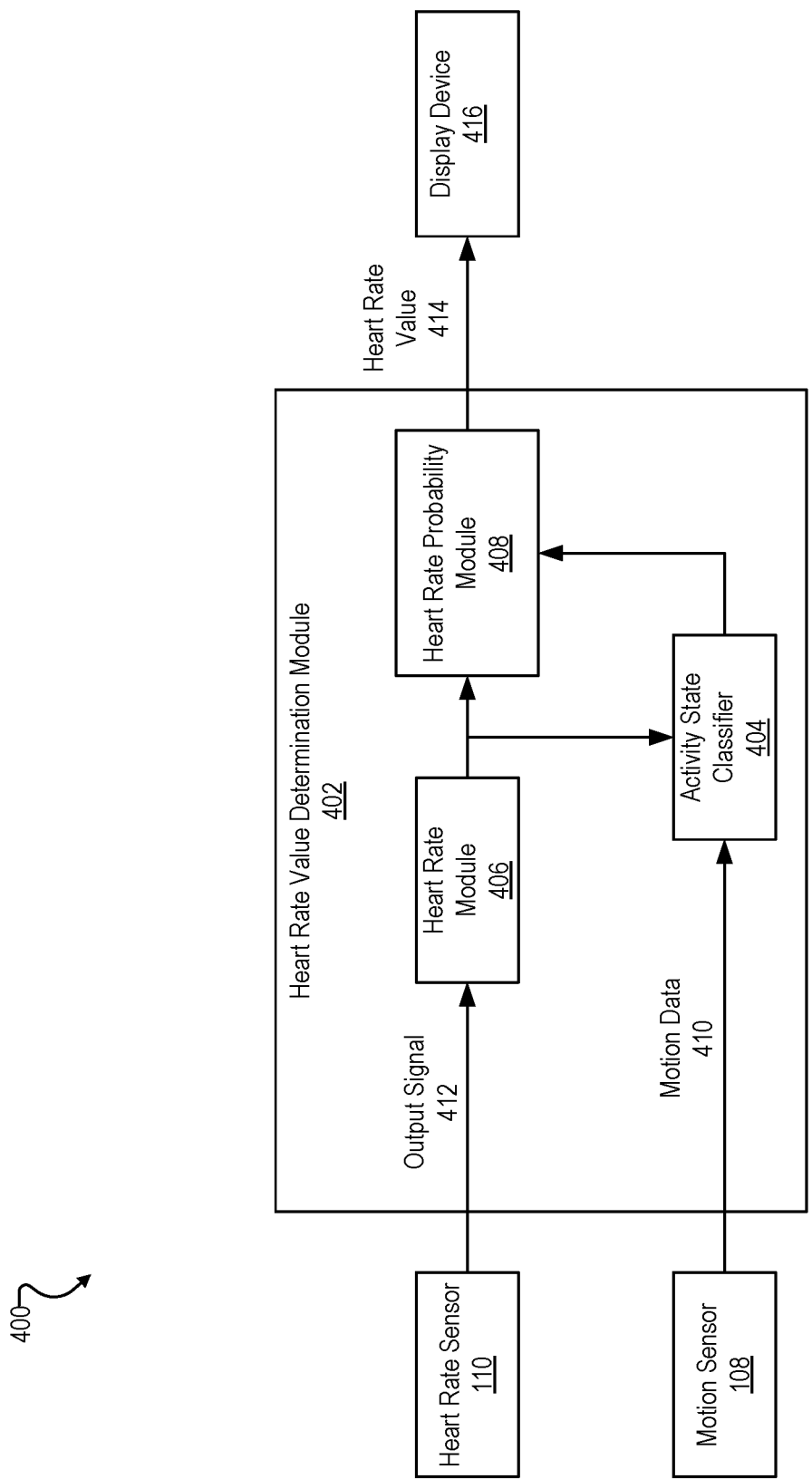
FIG. 4 shows an illustrative implementation of a heart rate value determination module that may be incorporated into a hearing system.

As an illustrative example, FIG. 4 shows an implementation 400 of a heart rate value determination module 402 that may be implemented by a hearing system according to the principles described herein and configured to determine a heart rate value based on a heart rate probability distribution function associated with motion of the user. As shown, heart rate value determination module 402 may include an activity state classifier 404, a heart rate module, 406, and a heart rate probability module 408. Heart rate value determination module 402 may include additional or alternative components as may serve a particular implementation.

Activity state classifier 404 of heart rate value determination module 402 may be configured to receive motion data 410 generated by motion sensor 108 and to determine, based on the received motion data 410, an activity state of the user.

In some implementations, the activity state determined by activity state classifier 404 may include an intensity of an activity performed by the user. As an example, the intensity of the activity as performed by the user may be determined based on a frequency and/or amplitude of the motion data 410. To illustrate, motion data 410 may indicate the user performing an activity of low or high intensity or of various levels of the intensity depending on a frequency and/or an amplitude of the detected motions. As another example, the intensity of the activity as performed by the user may be determined based on a duration in which motion data 410 lies within a defined range of frequency and/or amplitude, e.g. below or above a frequency and/or amplitude threshold or between various levels of frequency and/or amplitude thresholds. To illustrate, the longer the duration of a rather large frequency and/or amplitude of motion data 410, the larger the intensity of the activity may be determined.

In some implementations, the determined activity state may include a level of stress (e.g., physical or mental stress) of the user. As an example of physical stress, motion data 410 indicating a high level of intensity of the activity performed by the user and/or having a high frequency and/or amplitude may indicate a high level of physical stress to the user. Such high levels of physical stress may be representative of the user performing a physical activity. Alternatively, motion data 410 indicating a low level of intensity of the activity performed by the user and/or having a high frequency and/or amplitude may indicate a low level of physical stress to the user, which may be representative of the user not performing a physical activity. In some instances, the determined level of stress may include a duration of the stress and/or a period of recovery time after the stress has been detected based on motion data 410.

In some implementations, the activity state determined by activity state classifier 404 may include a type of activity that the user is performing. For example, activity state classifier 404 may be configured to classify motion data 410 with regard to at least one activity type or a plurality of different activity types. For example, activity state classifier 404 may be configured to determine whether motion data 410 matches a motion pattern associated with a respective activity type. E.g., one or more types of the activity may include at least one of a sedentary activity, light household work, walking, running, swimming, bicycling, driving a car, dancing, chewing, talking, or the like. In some instances, the type of the activity may be associated with a high level of physical stress to the user as a type of high intensity activity (e.g., running, jogging, dancing, etc.), a moderate level of physical stress to the user as a type of moderate intensity activity (e.g., walking, swimming, etc.), and/or a low level of physical stress to the user as a type of low intensity activity (e.g., sitting, standing, laying down, etc.). In some implementations, activity state classifier 404 may be configured to classify a type of activity that the user may perform during daily life (e.g., cleaning, vacuuming, washing dishes, gardening, etc.). Such daily activities may, in some instances, have a moderate to low frequency (e.g., motion data 410 having a frequency of less than about 70 individual movements per minute). Activity state classifier 404 may further be configured to classify a posture of the user as a type of activity.

Activity state classifier 404 may further be configured to determine a change in the activity state. For example, activity state classifier may be configured to determine a change in the level of stress to the user, a change in the intensity and/or type of activity that the user is performing, and/or a change in motion of the user (e.g., a change in posture).

In some implementations, activity state classifier 404 may be configured to receive blood flow data of the user to determine the activity state based on the blood flow data in addition to motion data 410. The blood flow sensor may be implemented by any suitable sensor configured to detect a property of blood flowing through vessels of the user and output blood flow data representative of a blood property (e.g., a blood pressure, a respiratory rate, a heart rate, a heart rate variability, a blood analyte level, a capillary oxygen saturation, and/or the like). For instance, the blood flow sensor may include an optical sensor (e.g., a photoplethysmography (PPG) sensor), which may be implemented as heart rate sensor 110. For example, heart rate module 406 of heart rate value determination module 402 may receive output signal 412 representative of the blood flow data generated by heart rate sensor 110. Heart rate module 406 may be configured to process output signal 412 generated by heart rate sensor 110 and output the processed output signal to activity state classifier 404. Accordingly, activity state classifier 404 may determine the activity state of the user based on the processed output signal of the user. In some implementations, output signal 412 may be processed in a frequency domain. To illustrate, a level of stress may be determined at a higher accuracy when taking into account the blood flow data and/or a blood property derived therefrom, which can be indicative of both physical and mental stress, whereas inertial sensor data 412 may be mostly representative of physical stress.

In some implementations, activity state classifier 404 may be configured to receive an audio signal detected by microphone 106 of hearing device 102 to further determine the activity state of the user based the received audio signal. For example, the audio signal may include audio content (e.g., music, speech, noise, etc.) generated by one or more audio sources included in an environment of the user. Such audio signals may allow activity state classifier 404 to determine a type of activity that the user is performing. For example, activity state classifier 404 may determine that a user is eating and/or drinking when the audio signal includes audio content representative of the user eating and/or drinking (e.g., chewing, swallowing, a sound of a coffee machine, etc.). Additionally or alternatively, the level of mental stress of the user may be determined based on the received audio signal. For example, the audio signal may include audio content having loud and/or stressful sounds (e.g., yelling, loud music, action in a television scene, etc.) that may indicate a high level of mental stress to the user. Alternatively, the audio signal may include audio content having soft and/or soothing sounds (e.g., soft music, meditation, etc.) that may indicate a low level of mental stress to the user.

In some implementations, the audio signal may further include an own voice content representative of an activity of the user's own voice. E.g., hearing device 102 may comprise a voice activity detector (VAD) configured to identify the user's own voice in the audio signal detected by microphone 106 and to provide own voice data representative of the user's own voice to activity state classifier 404. Activity state classifier 404 may be configured to determine the activity state of the user based on the own voice content in the audio signal, e.g. based on the own voice data. To illustrate, the user yelling and/or speaking fast may indicate a high level of mental stress to the user. The user being quiet and/or talking with a calm voice may indicate a low level of mental stress to the user. The own voice content may also be employed to improve identifying an intensity and/or type of activity performed by the user.

In some implementations, the audio signal may further include a voice input from the user. This may allow the user to vocalize a status and/or activity that the user is performing. For example, the user may vocalize when the user is performing an activity. In some implementations, the hearing system may be configured to request voice input from the user regarding the activity state of the user (e.g., by a mobile device or other user interface). Activity state classifier 404 may further be configured to determine a level of mental stress of the user based on the voice input received from the user (e.g., by voice analysis, vocal biomarkers, etc.).

In some implementations, activity state classifier 404 may be configured to receive data representative of a respiratory rate of the user to further determine the activity state of the user based on the respiratory rate. For example, a respiratory rate of the user may be determined by heart rate module 406 based on output signal 412 generated by heart rate sensor 110. Alternatively, a respiratory rate of the user may be detected by a separate device (e.g., a respirator) communicatively coupled with the hearing system.

In some implementations, activity state classifier 404 may be configured to receive data representative of a body temperature of the user to further determine the activity state of the user based on the body temperature. For example, a body temperature of the user may be determined by heart rate module 406 based on output signal 412 generated by heart rate sensor 110. Alternatively, a body temperature of the user may be detected by a separate device (e.g., a thermal sensor) communicatively coupled with the hearing system.

Still other suitable configurations and/or methods may be used by activity state classifier 404 to determine an activity state of the user. For example, activity state classifier 404 may be configured to receive data representative of a location of the user (e.g., by a global positioning system (GPS)) and/or a time of day (e.g., by a clock) for determining the activity state of the user. In some implementations, activity state classifier 404 may be configured to learn various activity states of the user over time based on previous data received by activity state classifier 404 while in the various activity states.

Heart rate probability module 408 may be configured to receive data representative of the determined activity state of the user from activity state classifier 404. Heart rate probability module 408 may be further configured to determine a heart rate probability distribution function based on the determined activity state. Determining the heart rate probability distribution function from the activity state may comprise selecting the heart rate probability distribution function from a plurality of heart rate probability distribution functions depending on the activity state. E.g., the plurality of heart rate probability distribution functions may be stored in memory 114 and accessed by processor 116 depending on the motion data and/or activity state. Determining the heart rate probability distribution function from the motion data and/or activity state may also comprise calculating the heart rate probability distribution function based on at least one parameter derived from the motion data and/or activity state, e.g. derived from the frequency and/or amplitude of the motion data and/or from the activity state of the user determined based on the motion data. To illustrate, at least one parameter (e.g. a mean value and/or a variance and/or a standard deviation) of a computable distribution function (e.g. a Gaussian distribution and/or a Laplacian distribution and/or a superposition of multiple distribution functions) may be derived from the motion data and/or activity state, and the distribution function may be calculated based on this parameter.

In some instances, the heart rate probability distribution function is provided as a continuous function, e.g. as a heart rate probability density function. In some instances, the heart rate probability distribution function is provided as a discrete function formed by a plurality of distinct functional values, e.g. by a number of different potential heart rate values associated with a respective probability of occurrence. In some instances, the heart rate probability distribution function can be converted from a continuous function to a discrete function, e.g. when performing a fast Fourier transform (FFT) for a processing of the output signal of the heart rate sensor in a frequency domain. In some instances, the heart rate probability distribution function can be converted from a discrete function to a substantially continuous function, e.g. by an interpolation between neighboring discrete functional values to provide an arbitrary number of intermediate functional values.

The heart rate probability distribution function may include a plurality of potential heart rate values for the user associated with a probability of occurrence of each potential heart rate value depending on the determined activity state. The activity state can thus be associated with the heart rate probability distribution function indicating a respective probability of occurrence of the potential heart rate values relative to the determined activity state. For example, the probability of occurrence of a resting or low heart rate value may be higher in an activity state having a low intensity and/or stress level than an activity state having a high intensity and/or stress level. Alternatively, the probability of occurrence of a high heart rate value may be higher in an activity state having a high intensity and/or stress level than an activity state having a low intensity and/or stress level. Correspondingly, a heart rate probability distribution function associated with the activity state having a high intensity and/or stress level may have a larger mean value as compared to a heart rate probability distribution function associated with the activity state having a low intensity and/or stress level. Moreover, the probability of occurrence of a high heart rate value may be subject to larger fluctuations in an activity state having a high intensity and/or stress level than in an activity state having a low intensity and/or stress level. Correspondingly, a heart rate probability distribution function associated with the activity state having a high intensity and/or stress level may have a larger variance as compared to a heart rate probability distribution function associated with the activity state having a low intensity and/or stress level.

In some implementations, heart rate probability module 408 may be configured to fit the probability of occurrence of each potential heart rate value of the heart rate probability distribution function to a Gaussian distribution (e.g., a normal distribution curve). The probability of occurrence of each potential heart rate value of the heart rate probability distribution function may be based on previous heart rate values in the activity state from the user and/or other users and/or based on previous heart rate values determined in conjunction with corresponding motion data and/or a corresponding activity state of the user and/or other users. Additionally or alternatively, the probability of occurrence of each potential heart rate value of the heart rate probability distribution function may be based on one or more characteristics of the user (e.g., age, gender, preconditions, body mass index, fitness level, cardiorespiratory properties, etc.) and/or of suitable population statistics as gained from other users.

To illustrate, a heart rate probability distribution function associated with a certain activity state may be produced by collecting a number of previous heart rate values associated with a comparable activity state (e.g. from a single user or a number of different users) and assigning the previous heart rate values to a respective probability of occurrence (e.g.

depending on how often a respective heart rate value has been observed within the collection of previous heart rate values). In some instances, those probabilities of occurrence associated with the previous heart rate values may be fitted to a type of a probability distribution function, e.g. a Gaussian distribution and/or a Laplacian distribution and/or a superposition of multiple distribution functions, to yield a, e.g. continuous, heart rate probability distribution function. In some instances, those probabilities of occurrence associated with the previous heart rate values may be directly employed as a heart rate probability distribution function, which e.g. may consist of distinct values. In some instances, those probabilities of occurrence associated with the previous heart rate values may be interpolated to determine the probabilities of occurrence of intermediate heart rate values in the heart rate probability distribution function, e.g. to provide a substantially continuous heart rate probability distribution function. Still other suitable configurations and/or methods for determining the heart rate probability distribution function may be used.

In some instances, activity state classifier 404 may be omitted such that heart rate probability module 408 may be configured to determine the heart rate probability distribution function directly from motion data 410 generated by motion sensor 108. For instance, the heart rate probability distribution function may be directly determined depending on a frequency and/or amplitude of the motion data. To illustrate, a heart rate probability distribution function associated with motion data having a large amplitude and/or frequency may have a larger mean value as compared to a heart rate probability distribution function associated with motion data having a small amplitude and/or frequency. Correspondingly, a heart rate probability distribution function associated with motion data having a large amplitude and/or frequency may have a larger variance as compared to a heart rate probability distribution function associated with the motion data having a small amplitude and/or frequency. E.g., producing a heart rate probability distribution function associated with certain motion data may comprise collecting a number of previous heart rate values associated with comparable motion data, e.g. from a single user or a number of different users, and assigning the previous heart rate values to a respective probability of occurrence.

In some implementations, heart rate probability module 408 may be configured to determine the heart rate probability distribution function based on the motion data, e.g. based on the activity state, depending on a probability determination criterion defining a dependency of the heart rate probability distribution function from the motion data, e.g. from the activity state. The probability determination criterion may be set based on at least one characteristic of the user. To illustrate, the heart rate probability distribution function may not only depend on the motion data but also on one or more user user-specific characteristics, which may thus be taken into account when determining the heart rate probability distribution function. Such a heart rate probability distribution function associated with a user-specific characteristic may be produced by collecting a number of previous heart rate values associated with comparable motion data and/or a comparable activity state from a number of different users with a corresponding user-specific characteristic, and assigning the previous heart rate values to a respective probability of occurrence. The resulting heart rate probability distribution function may then be associated with the motion data, e.g., the activity state, and the characteristic of the user.

The characteristic of the user may comprise, e.g., an age, a body mass index (BMI), a gender, a precondition, a fitness level, and/or a cardiorespiratory property of the user. The cardiorespiratory property of the user may comprise any property related to the respiratory system of the user and/or any cardiovascular property, e.g., a maximum heart rate, a resting heart rate, a maximal oxygen saturation (VO2max), a capillary oxygen saturation (SpO2), a blood pressure, and/or a respiration rate. The characteristic of the user may be determined, e.g., from data input via a user interface and/or a measurement performed on the user, e.g. by the heart rate sensor. To illustrate, an age, a body mass index (BMI), a gender and/or a precondition may be entered by the user via a user interface. A fitness level and/or a cardiorespiratory property of the user may be determined based on a measurement performed on the user, e.g. by the heart rate sensor. For instance, the user may be instructed to perform a fitness test and/or to relax for a certain time interval in order to measure the fitness level and/or the cardiorespiratory property, e.g., a maximum heart rate and/or a resting heart rate. Before determining the heart rate probability distribution function based on the motion data, e.g. based on the activity state, heart rate probability module 408 may be configured to set the probability determination criterion based on the characteristic of the user. The heart rate probability distribution function may thus be determined based on the motion data, e.g. the activity state, and the characteristic of the user.

Heart rate probability module 408 may be further configured to determine a heart rate value 414 for the user. For example, heart rate probability module 408 may be configured to receive the processed output signal from heart rate module 406. In some implementations, heart rate module 406 may be configured to identify a plurality of potential heart rate values from the processed output signal. Heart rate probability module 408 may be configured to determine heart rate value 414 depending on the probability of occurrence of each of the plurality of potential heart rate values in the heart rate probability distribution function associated with the determined activity state and/or motion data, as will be discussed in more detail below. Heart rate probability module 408 may further be configured to output heart rate value 414 to a display device 416 (e.g., a watch, mobile device, etc.) to display heart rate value 414 to the user. In some implementations, display device 416 may be configured to display a plot of heart rate value 414 over time. In some implementations, heart rate probability module 408 may be configured to determine heart rate value 414 by selecting a heart rate value from the plurality of potential heart rate values identified by heart rate module 406 depending on the probability of occurrence in the heart rate probability distribution function.

Figure 5A:
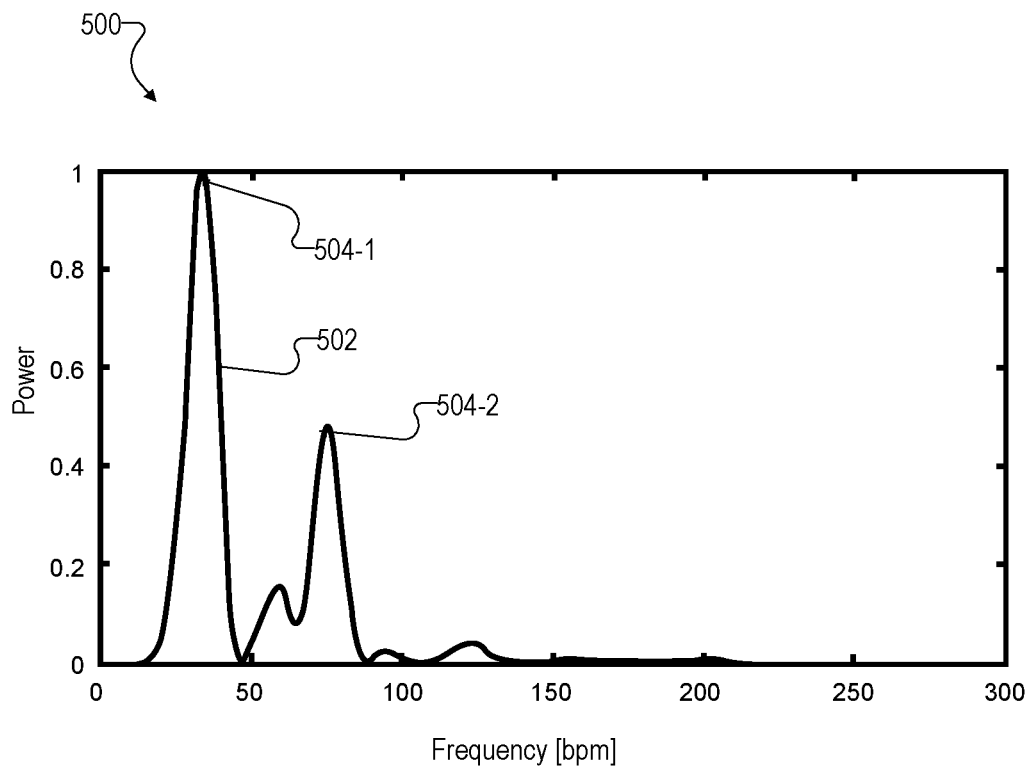
FIG. 5A shows an illustrative implementation of a processed output signal.

As an illustrative example, FIG. 5A shows an implementation 500 of a processed output signal 502 (e.g., output signal 412 processed by heart rate module 406). As shown, processed output signal 502 may include a plurality of potential heart rate values 504 (e.g., heart rate values 504-1 to 504-2 shown as peaks in processed output signal 502). E.g., heart rate probability module 408 may be configured to identify potential heart rate values 504-1, 504-2 in output signal 502) by identifying a respective peak in output signal 502 (e.g. by employing a peak detection algorithm). Potential heart rate values 504-1, 504-2 may be indicative of an amplitude associated with a respective level of a heart rate. In the illustrated example, the level of the heart rate is shown on an axis of abscissa as a frequency, in units of beats per minute (bpm). The amplitude is shown over an axis of ordinate as a power of the output signal 502. Output signal 502 is plotted over the axis of abscissa and the axis of ordinate. The potential heart rate values may be defined as peaks 504-1, 504-2 as determined in the output signal 502, e.g. in terms of the level of the heart rate and the amplitude of output signal 502 at the respective peak 504-1, 504-2.

Figure 5B:
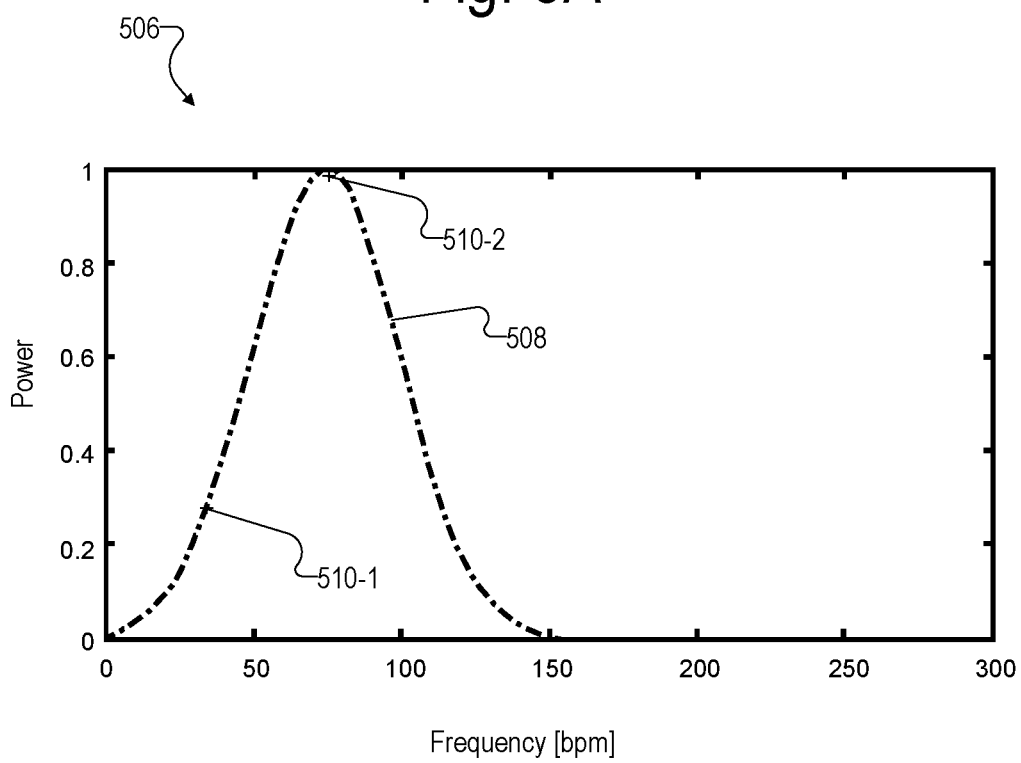
FIG. 5B shows an illustrative implementation of a heart rate probability distribution function.

FIG. 5B shows an illustrative implementation 506 of heart rate probability distribution function 508 associated with the motion data and/or the determined activity state. For example, heart rate probability distribution function 508 may include a plurality of potential heart rate values for the user associated with the motion data, e.g., in the determined activity state, based on a probability of occurrence of each potential heart rate values relative to the motion data, e.g., in the determined activity state. In the illustrated example, heart rate probability distribution function 508 is continuously plotted over an axis of abscissa indicating a level of the heart rate and an axis of ordinate indicating a probability of occurrence of potential heart rate values. For illustrative purposes, output signal 502 and heart rate probability distribution function 508 illustrated in FIGS. 5A-B are normalized with respect to each other, e.g. by setting potential heart rate value 504-1 having the largest amplitude in the output signal 502 illustrated in FIG. 5A corresponding to a maximum value of heart rate probability distribution function 508 illustrated in FIG. 5B. Determining the heart rate value may be performed by heart rate probability module 408 with or without such a normalization.

In the illustrated example, a first potential heart rate value 504-1 of processed output signal 502 may have a first probability of occurrence 510-1 in heart rate probability distribution function 508. A second potential heart rate value 504-2 of processed output signal 502 may have a second probability of occurrence 510-2 in heart rate probability distribution function 508. Accordingly, heart rate probability module 408 may determine heart rate value 414 by selecting the potential heart rate value 504 having a maximum probability in heart rate probability distribution function 508. In the illustrated example, second probability 510-2 of second potential heart rate value 504-2 is higher than first probability 510-1 of first potential heart rate value 504-1 in heart rate probability distribution function 508. In such instances, heart rate probability module 408 may select second potential heart rate value 504-2 as heart rate value 414 of the user.

In some implementations, heart rate probability module 408 may be configured to determine heart rate value 414 by selecting a heart rate value from the plurality of potential heart rate values identified by heart rate module 406 further depending on an amplitude of the heart rate value in the output signal 412. E.g., the amplitude of the heart rate value may be a power level of the output signal 412, as illustrated above in conjunction with FIG. 5A. For instance, the heart rate value may be selected from potential heart rate values 504-1, 504-2 in output signal 502 depending on whether the probability of occurrence in the heart rate probability distribution function exceeds a threshold, and depending on whether the amplitude of the heart rate value in output signal 412 exceeds a threshold.

To illustrate, the amplitude of potential heart rate values 504-1, 504-2 selected from output signal 502 may be weighted, e.g. multiplied or otherwise combined, with the corresponding probability of occurrence in heart rate probability distribution function 508. E.g., the corresponding probability of occurrence in heart rate probability distribution function 508 may be determined at a level of the heart rate in heart rate probability distribution function 508 corresponding to the level of the heart rate of potential heart rate values 504-1, 504-2 in output signal 502. Thus, by linking the amplitude of potential heart rate values 504-1, 504-2 in output signal 502 with the probability of occurrence in heart rate probability distribution function 508, a weighted potential heart rate value may be generated for each of the potential heart rate values 504-1, 504-2.

Heart rate probability module 408 may then be configured to determine heart rate value 414 from the weighted potential heart rate values determined for each potential heart rate value 504-1, 504-2 in output signal 502. For example, heart rate probability module 408 may compare the weighted heart rate values and determine heart rate value 414 based on the comparison. E.g., heart rate probability module 408 may determine heart rate value 414 as the weighted heart rate value having the largest amplitude. As another example, heart rate probability module 408 may determine the weighted heart rate value having the largest amplitude being excluded based on an exclusion criterion, and then determine heart rate value 414 as the weighted heart rate value having the second largest amplitude, if not excluded based on another exclusion criterion. As a result, in the illustrated example, heart rate probability module 408 may also select second potential heart rate value 504-2 as heart rate value 414 of the user.

In some implementations, determining heart rate value 414 may include weighting, based on the heart rate probability distribution function, the plurality of potential heart rate values and determining, from the weighted potential heart rate values, the heart rate value. For instance, the amplitude of potential heart rate values 504-1, 504-2 may be weighted based on the probability of occurrence in heart rate probability distribution function 508. E.g., the amplitude of potential heart rate values 504-1, 504-2 may be a power level of the output signal 412, as illustrated above in conjunction with FIG. 5A. The weighting may comprise, e.g., linking the amplitude of potential heart rate values 504-1, 504-2 to a probability of occurrence in heart rate probability distribution function 508 by a mathematical operation and/or numerical algorithm performed by heart rate probability module 408, e.g. a multiplication, linear combination, nonlinear combination, correlation, convolution, and/or the like.

Weighting potential heart rate values 504-1, 504-2 may be performed before and/or after a processing of output signal 412, 502 to identify potential heart rate values 504-1, 504-2 from output signal 412, 502, e.g. by a peak detection algorithm, as described above in conjunction with FIG. 5A. In some instances, output signal 412, 502 may be weighted including potential heart rate values 504-1, 504-2 contained in output signal 412, 502. After the weighting, potential heart rate values 504-1, 504-2 may be identified in the weighted output signal 412, 502 as weighted potential heart rate values 504-1, 504-2. To illustrate, weighting the output signal 502 may comprise linking the amplitude of output signal 502 to the probability of occurrence in heart rate probability distribution function 508. Heart rate value 414 may then be determined by selecting heart rate value 414 from the weighted output signal depending on an amplitude of the potential heart rate values in the weighted output signal. For instance, heart rate value 414 may be determined by a peak detection in the weighted output signal and/or by a comparison of different weighted potential heart rate values identified in the weighted output signal. In some instances, heart rate value 414 may also be directly determined from the weighted output signal, e.g. without identifying the plurality of potential heart rate values 504-1, 504-2 from output signal 412, 502. To illustrate, heart rate value 414 may be determined from the weighted output signal as a maximum value of the weighted output signal In some instances, potential heart rate values 504-1, 504-2 may be identified from output signal 412, 502 before weighting potential heart rate values 504-1, 504-2 to provide for weighted potential heart rate values. E.g., the corresponding probability of occurrence in heart rate probability distribution function 508 may be determined at a level of the heart rate in heart rate probability distribution function 508 corresponding to the level of the heart rate of potential heart rate values 504-1, 504-2 in output signal 502. Thus, by linking the amplitude of potential heart rate values 504-1, 504-2 in output signal 502 with the probability of occurrence in heart rate probability distribution function 508, a weighted potential heart rate value may be generated for one or more or each of the potential heart rate values 504-1, 504-2.

Heart rate probability module 408 may then be configured to determine heart rate value 414 from the weighted potential heart rate values. For example, heart rate probability module 408 may compare the weighted potential heart rate values and determine heart rate value 414 based on the comparison. E.g., heart rate probability module 408 may determine heart rate value 414 as the weighted heart rate value having the largest amplitude. As another example, heart rate probability module 408 may determine the weighted heart rate value having the largest amplitude being excluded based on an exclusion criterion, and then determine heart rate value 414 as the weighted heart rate value having the second largest amplitude, if not excluded based on another exclusion criterion.

Figure 6:
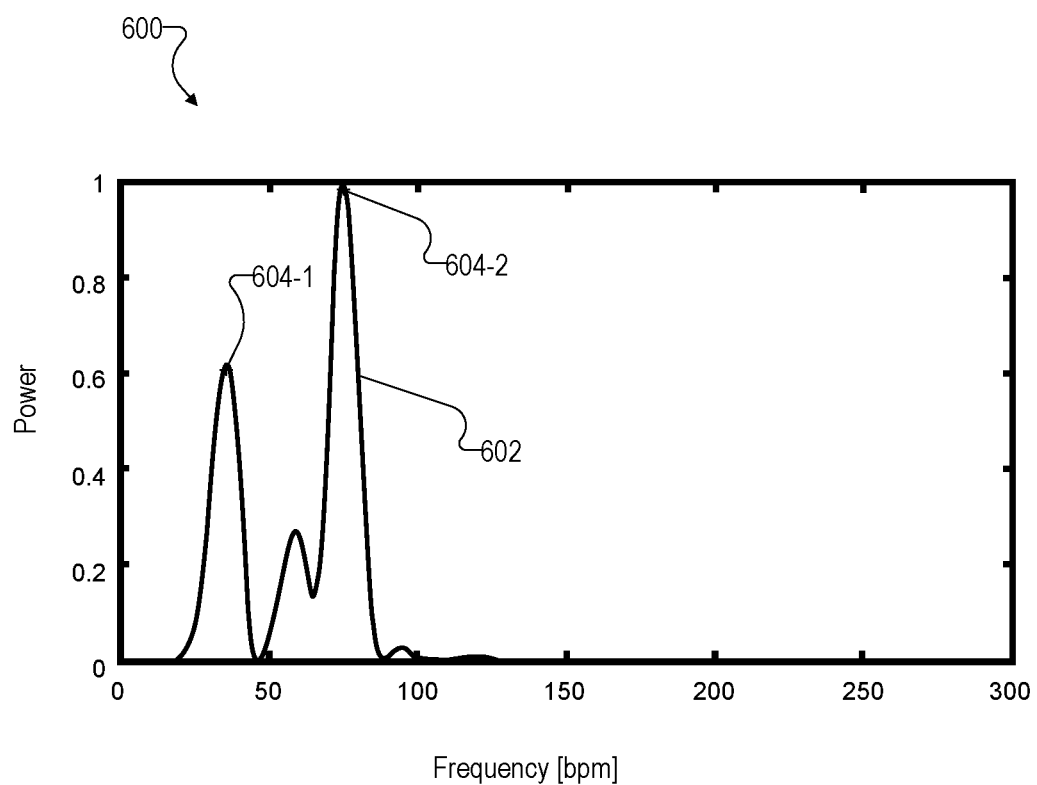
FIG. 6 shows an illustrative implementation of a weighted signal based on the output signal of FIG. 5A and the heart rate probability distribution function of FIG. 5B.

As an illustrative example, FIG. 6 shows an implementation 600 of a weighted signal 602 that may be generated by heart rate probability module 408 by weighting output signal 502 with heart rate probability distribution function 508. As shown, first potential heart rate value 504-1 of processed output signal 502 may be weighted by heart rate probability distribution function 508 to provide a first weighted heart rate value 604-1 in weighted signal 602. Second potential heart rate value 504-6 of processed output signal 502 may be weighted by heart rate probability distribution function 508 to provide a second weighted heart rate value 604-2 in weighted signal 602. Because second weighted heart rate value 604-2 is greater than first weighted heart rate value 604-1, heart rate probability module 408 may select second weighted heart rate value 604-2 as heart rate value 414 of the user.

Still other suitable configuration and/or methods for determining heart rate value 414 may be used. For example, in some implementations, heart rate probability module 408 may be configured to average, or otherwise combine, the potential heart rate values and/or the probabilities of occurrence of the potential heart rate values in the heart rate probability distribution function. Additionally or alternatively, heart rate probability module 408 may be configured to update the heart rate probability distribution function to include the determined heart rate value 414 in the heart rate probability distribution function. Heart rate probability module 408 may further be configured to learn heart rate values 414 of the user for various activity states over time.

In the illustrated examples, heart rate probability module 408 selected a potential heart rate value (e.g., 504-2) that had an initially lower peak value than another potential heart rate value (e.g., 504-1) as the determined heart rate value 414 because the selected potential heart rate value (e.g., 504-2) had a greater probability of occurrence. This may provide a more accurate heart rate value 414 for the user.

In some implementations, after determining heart rate value 414 for the user, probability module 408 may be configured to update the heart rate probability distribution function based on the determined heart rate value 414. The updating of the heart rate probability distribution function may comprise setting a new value of the probability of occurrence of the potential heart rate value in the probability distribution function, which potential heart rate value corresponds to the determined heart rate value 414. E.g., the heart rate probability distribution function may be updated such that the probability of occurrence of the potential heart rate value which corresponds to the determined heart rate value has an increased value in the heart rate probability distribution function. To illustrate, a heart rate value 414 determined for the user may indicate a higher probability that the same heart rate value 414 may occur again in the future for the same user in the respective activity state and/or relative to the associated motion data. The higher probability of occurrence can thus be taken into account by the updating of the heart rate probability distribution function.

In some instances, motion of the user may affect the accuracy or quality of output signal 412 generated by heart rate sensor 110. For example, motion artifacts caused by motion of the user may be included in output signal 412 that may artificially increase a peak value of one or more potential heart rate values in output signal 412. By determining heart rate value 414 based on a probability of the heart rate value in the activity state, heart rate value determination module 402 may determine a more accurate heart rate value 414 by filtering and/or removing such motion artifacts.

In some implementations, heart rate value determination module 402 may be further configured to determine, based on motion data 410 and/or output signal 412, a signal quality metric of output signal 412. For example, motion data 410 having a high intensity and/or frequency may result in a signal quality metric having a low value to indicate a low-quality output signal 412. Alternatively, motion data 410 having a low intensity and/or frequency may result in a signal quality metric having a high value to indicate a high-quality output signal 412. Further, a large number of distinct peaks in output signal 412 and/or a small amplitude of the peaks relative to a background signal may also indicate a signal quality metric having a low value. E.g., the large number of distinct peaks can be caused by a motion of the user, as described above.

Heart rate value determination module 402 may further be configured to execute the updating of the heart rate probability distribution function based on the determined heart rate value 414, as described above, depending on the signal quality metric. For instance, the updating of the heart rate probability distribution function may be only performed when the signal quality metric exceeds a threshold, e.g. to assure a minimum quality of the output signal 412 defined by the threshold. To illustrate, when the output signal 412 has a rather low quality, the determined heart rate value 414 may be less reliable. Updating of the heart rate probability distribution function may thus be avoided under those circumstances to prevent a distortion of the heart rate probability distribution function by inaccurate or false probability values.

Heart rate value determination module 402 may further be configured to determine, based on the signal quality metric and the heart rate probability distribution function, a probability of occurrence of the determined heart rate value, and associate the determined heart rate value with the determined probability in the heart rate probability distribution function. For example, a heart rate value determined based on motion data 410 having a low signal quality metric may be associated with a low probability of occurrence. Alternatively, a heart rate value determined based on motion data 410 having a high signal quality metric may be associated with a high probability of occurrence. In some implementations, heart rate value determination module 402 may determine whether to include the determined heart rate value in the heart rate probability distribution function based on the signal quality metric. For example, heart rate value determination module 402 may not include a determined heart rate value having a low signal quality metric in the heart rate probability distribution function.

In some implementations, heart rate value determination module 402 may perform, based on motion data 410, an operation with respect to hearing device 102. For example, when motion data 410 (e.g., a frequency and/or intensity of motion data 410) is above a threshold to indicate a low signal quality, heart rate value determination module 402 may abstain from receiving output signal 412 generated by heart rate sensor 110. Additionally or alternatively, when motion data 410 is above a threshold, heart rate value determination module 402 may disable heart rate sensor 110 and/or another device configured to measure heart rate data of the user.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM") or static random access memory ("SRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 7:
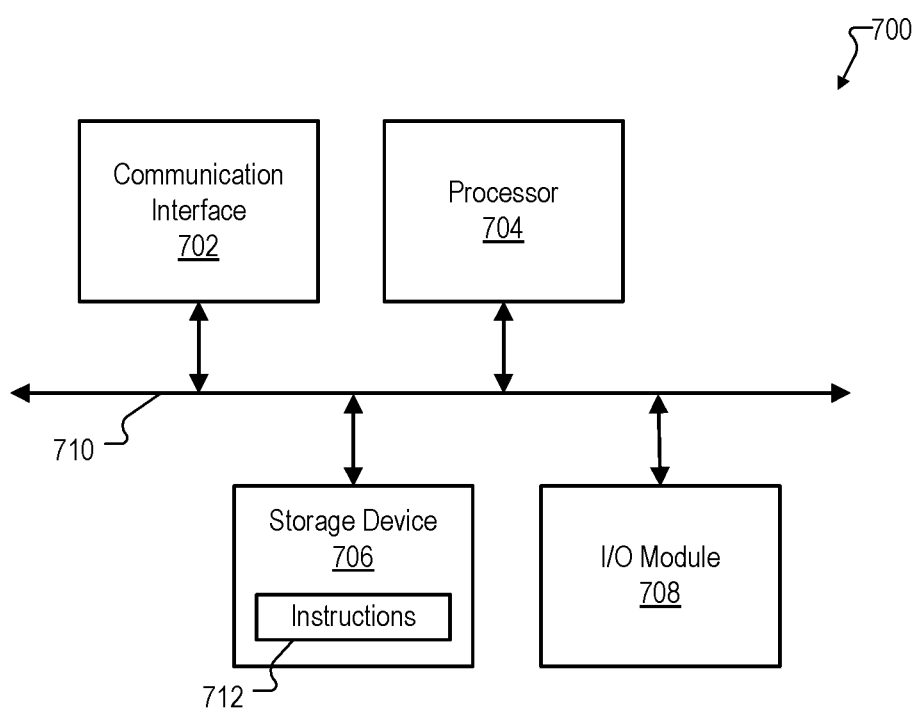
FIG. 7 shows an illustrative computing system according to the principles described herein.

FIG. 7 shows an illustrative computing device 700 that may be specifically configured to perform one or more of the processes described herein. Any of the systems, computing devices, and/or other components described herein may be implemented by computing device 700.

As shown in FIG. 7, computing device 700 may include a communication interface 702, a processor 704, a storage device 706, and an input/output ("I/O") module 708 communicatively connected one to another via a communication infrastructure 710. While an illustrative computing device 700 is shown in FIG. 7, the components illustrated in FIG. 7 are not intended to be limiting. Additional or alternative components may be used in other embodiments. Components of computing device 700 shown in FIG. 7 will now be described in additional detail.

Communication interface 702 may be configured to communicate with one or more computing devices. Examples of communication interface 702 include, without limitation, a wired network interface (such as a network interface card), a wireless network interface (such as a wireless network interface card), a modem, an audio/video connection, and any other suitable interface.

Processor 704 generally represents any type or form of processing unit capable of processing data and/or interpreting, executing, and/or directing execution of one or more of the instructions, processes, and/or operations described herein. Processor 704 may perform operations by executing computer-executable instructions 712 (e.g., an application, software, code, and/or other executable data instance) stored in storage device 706.

Storage device 706 may include one or more data storage media, devices, or configurations and may employ any type, form, and combination of data storage media and/or device. For example, storage device 706 may include, but is not limited to, any combination of the non-volatile media and/or volatile media described herein. Electronic data, including data described herein, may be temporarily and/or permanently stored in storage device 706. For example, data representative of computer-executable instructions 712 configured to direct processor 704 to perform any of the operations described herein may be stored within storage device 706. In some examples, data may be arranged in one or more databases residing within storage device 706.

I/O module 708 may include one or more I/O modules configured to receive user input and provide user output. I/O module 708 may include any hardware, firmware, software, or combination thereof supportive of input and output capabilities. For example, I/O module 708 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 708 may include one or more devices for presenting output to a user, including, but not limited to, a graphics engine, a display (e.g., a display screen), one or more output drivers (e.g., display drivers), a vibration motor, one or more audio speakers, and one or more audio drivers. In certain embodiments, I/O module 708 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    receiving, from a motion sensor included in a hearing device configured to be worn by a user, motion data representative of motion of the user while the user wears the hearing device;
    receiving an output signal generated by a heart rate sensor in contact with the user;
    receiving an audio signal detected by a microphone included in the hearing device;
    determining, based on the motion data and the audio signal, a heart rate probability distribution function, the heart rate probability distribution function indicative of a probability of occurrence of potential heart rate values; and
    determining, based on the output signal and the heart rate probability distribution function, a heart rate value for the user, wherein the determining the heart rate value comprises selecting the heart rate value from a plurality of potential heart rate values included in the output signal based on the probability of occurrence of each potential heart rate value in the heart rate probability distribution function.

2. The method of claim 1, wherein the output signal is processed in a frequency domain.

3. The method of claim 1, wherein the determining the heart rate value comprises:
    weighting, based on the heart rate probability distribution function, one or more potential heart rate values included in the output signal; and
    determining, from the weighted potential heart rate values, the heart rate value.

4. The method of claim 3, wherein the heart rate value is determined by selecting the heart rate value from the weighted potential heart rate values depending on an amplitude of the weighted potential heart rate values.

5. The method of claim 1, further comprising updating the heart rate probability distribution function based on the determined heart rate value of the user.

6. The method of claim 5, further comprising determining, based on one or both of the motion data or the output signal of the heart rate sensor, a signal quality metric of the output signal, wherein the updating of the heart rate probability distribution function is executed depending on the signal quality metric.

7. The method of claim 1, further comprising setting a probability determination criterion defining a dependency of the heart rate probability distribution function from the motion data and the audio signal such that the heart rate probability distribution function can be determined from the motion data and the audio signal depending on the probability determination criterion, wherein the probability determination criterion is set based on a characteristic of the user.

8. The method of claim 7, wherein the characteristic of the user is determined from one or both of data input via a user interface or a measurement performed on the user by the heart rate sensor.

9. The method of claim 7, wherein the characteristic of the user comprises at least one of: an age of the user, a body mass index of the user, a gender of the user, a precondition of the user, a fitness level of the user, and a cardiorespiratory property of the user.

10. The method of claim 1, wherein the heart rate probability distribution function is determined from the motion data and the audio signal by one or both of:
    selecting the heart rate probability distribution function from a plurality of heart rate probability distribution functions depending on the motion data and the audio signal; or
    calculating the heart rate probability distribution function based on at least one parameter derived from the motion data and the audio signal.

11. The method of claim 1, further comprising performing, based on the motion data, an operation with respect to the hearing device.

12. The method of claim 11, wherein, when the motion data is above a threshold, the operation comprises abstaining from receiving the output signal generated by the heart rate sensor.

13. The method of claim 11, wherein, when the motion data is above a threshold, the operation comprises disabling the heart rate sensor configured to measure heart rate data of the user.

14. The method of claim 1, wherein the selecting the heart rate value is based on normalizing the output signal relative to the heart rate probability distribution function.

15. The method of claim 1, further comprising determining, based on the motion data and the audio signal, an activity state of the user, wherein the determining the heart rate probability distribution function is based on the activity state of the user.

16. The method of claim 15, wherein the activity state is indicative of at least one of: an intensity of an activity performed by the user; a type of an activity performed by the user; or a level of stress to the user.

17. The method of claim 15, wherein the heart rate probability distribution has one or both of a mean value or a variance that is dependent on the activity state.

18. A system comprising:
    a hearing device configured to be worn by a user and comprising a motion sensor; and
    a processing unit communicatively coupled to the motion sensor and configured to:
        receive, from the motion sensor, motion data representative of motion of the user while the user wears the hearing device;
        receive an output signal generated by a heart rate sensor in contact with the user;
        receive an audio signal detected by a microphone included in the hearing device;
        determine, based on the motion data and the audio signal, a heart rate probability distribution function, the heart rate probability distribution function indicative of a probability of occurrence of potential heart rate values; and
        determine, based on the output signal and the heart rate probability distribution function, a heart rate value for the user, wherein the determining the heart rate value comprises selecting the heart rate value from a plurality of potential heart rate values included in the output signal based on the probability of occurrence of each potential heart rate value in the heart rate probability distribution function.

19. A hearing device configured to be worn by a user, the hearing device comprising:
    a motion sensor;
    a heart rate sensor;
    a microphone; and
    a processing unit communicatively coupled to the motion sensor and the heart rate sensor, the processing unit configured to:
        receive, from the motion sensor, motion data representative of motion of the user while the user wears the hearing device;

receive an output signal generated by the heart rate sensor in contact with the user while the user wears the hearing device;

receive an audio signal detected by the microphone while the user wears the hearing device;

determine, based on the motion data and the audio signal, a heart rate probability distribution function, the heart rate probability distribution function indicative of a probability of occurrence of potential heart rate values; and determine, based on the output signal and the heart rate probability distribution function, a heart rate value for the user, wherein the determining the heart rate value comprises selecting the heart rate value from a plurality of potential heart rate values included in the output signal based on the probability of occurrence of each potential heart rate value in the heart rate probability distribution function.

* * * * *